United States Patent
Sutter et al.

(10) Patent No.: US 6,168,718 B1
(45) Date of Patent: Jan. 2, 2001

(54) METHOD FOR PURIFYING BLOOD PLASMA AND APPARATUS SUITABLE THEREFOR

(75) Inventors: Mark Alexander Sutter, Dexter; Noel Tod Borton, Chelsea, both of MI (US); Daniel F. Bischof, McHenry, IL (US); John Chapman, Lake Villa, IL (US); Robert E. Herman, Lindenhurst, IL (US); Chong-Son Sun, Lake Forest, IL (US)

(73) Assignee: Pall Corporation, East Hills, NY (US)

( * ) Notice: Under 35 U.S.C. 154(b), the term of this patent shall be extended for 0 days.

(21) Appl. No.: 09/500,794

(22) Filed: Feb. 10, 2000

Related U.S. Application Data

(63) Continuation of application No. 09/280,517, filed on Apr. 5, 1999, now abandoned, which is a continuation of application No. 08/841,163, filed on Apr. 29, 1997, now abandoned, which is a continuation of application No. 08/745,948, filed on Nov. 8, 1996, now abandoned.

(51) Int. Cl.[7] .............................. B01D 37/00; B01D 61/00
(52) U.S. Cl. .......................... 210/651; 210/436; 210/472; 210/483; 210/488; 210/489; 210/490; 210/650; 210/767; 435/2
(58) Field of Search .................................. 210/435, 483, 210/488, 489, 490, 496, 500.21, 436, 650, 651, 767, 472; 422/101, 102; 435/2

(56) References Cited

U.S. PATENT DOCUMENTS

| | | | |
|---|---|---|---|
| 3,876,738 | 4/1975 | Marinaccio et al. | 264/41 |
| 4,025,618 | 5/1977 | Garber et al. | 424/101 |
| 4,246,107 | 1/1981 | Takenaka et al. | 210/806 |
| 4,340,479 | 7/1982 | Pall | 210/490 |
| 4,473,474 | 9/1984 | Ostreicher et al. | 210/636 |
| 4,673,504 | 6/1987 | Ostreicher et al. | 210/500.22 |
| 4,701,267 | 10/1987 | Watanabe et al. | 210/806 |
| 4,708,803 | 11/1987 | Ostreicher et al. | 210/650 |
| 4,711,793 | 12/1987 | Ostreicher et al. | 427/244 |
| 4,900,449 | 2/1990 | Kraus et al. | 210/651 |
| 4,915,683 | 4/1990 | Sieber | 604/4 |
| 4,925,572 | 5/1990 | Pall | 210/767 |
| 4,964,990 | 10/1990 | Kraus et al. | 210/490 |
| 4,985,153 | 1/1991 | Kuroda et al. | 210/782 |
| 5,023,052 | 6/1991 | Nagatomo et al. | 422/56 |
| 5,076,935 | 12/1991 | Kraus et al. | 210/651 |
| 5,089,146 | 2/1992 | Carmen et al. | 210/782 |
| 5,100,564 | 3/1992 | Pall et al. | 210/782 |
| 5,102,407 | 4/1992 | Carmen et al. | 604/410 |
| 5,108,607 | 4/1992 | Kraus et al. | 210/500.39 |
| 5,229,012 | 7/1993 | Pall et al. | 210/767 |
| 5,288,403 | 2/1994 | Ohno | 210/508 |
| 5,298,165 | 3/1994 | Oka et al. | 210/645 |
| 5,300,019 | 4/1994 | Bischof et al. | 604/4 |
| 5,387,187 | 2/1995 | Fell et al. | 604/6 |
| 5,399,268 | 3/1995 | Pall et al. | 210/767 |
| 5,403,272 | 4/1995 | Deniega et al. | 604/4 |
| 5,494,592 | 2/1996 | Latham, Jr. et al. | 210/805 |

(List continued on next page.)

FOREIGN PATENT DOCUMENTS

| | | |
|---|---|---|
| 0554460 | 8/1993 | (EP) . |
| 2037614 | 7/1980 | (GB) . |
| 9722245 | 6/1997 | (WO) . |
| 9818908 | 5/1998 | (WO) . |

*Primary Examiner*—John Kim
(74) *Attorney, Agent, or Firm*—Leydig, Voit & Mayer, Ltd.

(57) ABSTRACT

A method for purifying conventionally treated blood plasma to remove substantially all residual leukocytes while maintaining useful flow rates for medically useful amounts of plasma utilizes a disposable, heat-sterilizable filter employing one or more depth-type prefilters and at least one intermediate hydrophilic microporous membrane followed by at least one final hydrophilic microporous membrane having a smaller pore size than the intermediate membrane within a common housing. The purified plasma is preferably subjected to chemical treatment to destroy infectious agents such as hepatitis and HIV.

1 Claim, 3 Drawing Sheets

U.S. PATENT DOCUMENTS

| | | | |
|---|---|---|---|
| 5,498,336 | 3/1996 | Katsurada et al. | 210/496 |
| 5,501,795 | 3/1996 | Pall et al. | 210/508 |
| 5,512,187 | 4/1996 | Buchholz et al. | 210/767 |
| 5,536,238 | 7/1996 | Bischof | 604/6 |
| 5,536,413 | 7/1996 | Bormann et al. | 210/650 |
| 5,545,339 | 8/1996 | Boremann et al. | 210/806 |
| 5,545,516 | 8/1996 | Wagner | 435/2 |
| 5,549,834 | 8/1996 | Brown | 210/806 |
| 5,591,337 | 1/1997 | Lynn et al. | 210/489 |
| 5,607,579 | 3/1997 | Latham, Jr. et al. | 210/195.1 |
| 5,639,376 | 6/1997 | Lee et al. | 210/645 |
| 5,660,731 | 8/1997 | Piechocki et al. | 210/669 |
| 5,935,092 | 8/1999 | Sun et al. | 604/4 |

METHOD FOR PURIFYING BLOOD PLASMA AND APPARATUS SUITABLE THEREFOR

This application is a continuation application of U.S. Ser. No. 09/280,517, filed Apr. 5, 1999, abandoned, which is a continuation of U.S. Ser. No. 08/841,163, filed Apr. 29, 1997, abandoned which is a continuation of U.S. Ser. No. 08/745,948, filed Nov. 8, 1996, abandoned, which are each incorporated by reference.

TECHNICAL FIELD

The present invention pertains to a method for purifying blood plasma of white blood cells (leukocytes) and undesirable contaminants, particularly viral contaminants, and to an apparatus suitable for this use.

BACKGROUND ART

Plasma is the continuous liquid phase of blood which transports the necessary active substance which feed and maintain the body. Included within plasma are electrolytes, soluble sugars and proteins, and numerous enzymes, antigens, etc. While whole blood also contains red and white blood cells (erythrocytes and leukocytes), these components are substantially removed in the preparation of plasma. Plasma is frequently administered to patients who are seriously ill, for example burn victims. Plasma may also be fractionated to provide fractions enriched in certain components such as Factor VIII to treat many diseases, including Haemophilia.

Unfortunately, many disease-causing viruses, such as Hepatitis and HIV, may be transported by plasma if the blood donor has been infected by these diseases. Even without such infection, plasma may be contaminated during collection and subsequent processing. While centrifugation is effective to remove erythrocytes and the majority of leukocytes, infective viruses cannot generally be removed without resorting to ultracentrifugation. Such treatment is not generally cost effective and moreover may change the chemical make-up of the plasma by separation of larger molecules contained therein.

Administration of plasma containing even the most minor amounts of infectious agents can be catastrophic, and thus methods have been proposed to sterilize plasma utilizing chemical sterilizing agents. Unfortunately, if the plasma contains leukocytes which contain or are bound to infectious agents, these latter may not be destroyed by such processes, and thus a risk of infection is present. Virtually all leukocytes must therefore be removed.

Simple filtration of the plasma prior to chemical sterilization is problematic, as plasma is unique in the sense that in addition to low molecular weight species and electrolytes which may easily pass through even "tight" membranes, the larger protein species will rapidly form a polarized gel coating on the membrane should the pore size be too small. For example, the albumin fraction of human plasma contains prealbumin and albumin, with molecular weights in the 60,000 to 70,000 range, while fibrinogen, and various immunoglobulins have molecular weights in the range of 300,000 to $1 \times 10^6$. The β-lipoproteins, important in the transport of fats and lipids, have molecular weights in the range of $3 \times 10^6$ to $20 \times 10^6$.

When the plasma contains infectious agents such as viruses, the pore size necessary to completely remove these agents, particularly retroviruses, is such that the filter becomes rapidly clogged, thus requiring large filter area or repeated filter replacement. Clogging is particularly important with respect to the small but finite amount of leukocytes present in conventionally prepared plasma. Leukocytes are deformable, and may clog fine pores even though the leukocytes are physically larger than the pore. Further, and as indicated previously, a small pore size may also filter out desirable macromolecules contained in the plasma.

Leukocytes, which are positively charged, have been separated from plasma by membranes having charged sites. The ability to separate leukocytes in this fashion allows membranes with larger pore sizes to be used, as the removal is due to electrostatic attraction rather than physical separation. The larger pore size enhances the useful flow rate. Unfortunately, the charged membranes have a finite number of charged sites which limit their capacity. Moreover, the possibility exists that a given leucocyte may pass through the filter without encountering a charged site to bind it to the filtration medium. Random "pass through" cannot be tolerated in view of the danger of infection by agents such as hepatitis and HIV.

A suitable filter must not only be capable of removing leukocytes while allowing larger macromolecules to permeate the membrane, but must do so while processing a useful volume of plasma at a useful flow rate and acceptable pressure.

DISCLOSURE OF THE INVENTION

The subject invention pertains to a process for purifying blood plasma which has been subjected to centrifugation or filtration to remove erythrocytes and a substantial quantity of leukocytes, wherein all or substantially all the remainder of the residual leukocytes are removed through the use of a sterilizable multicomponent filter stack. The filter stack consists of a prefilter, a leukocyte retaining, intermediate hydrophilic membrane filter ("intermediate membrane") and a final, leukocyte retaining safety hydrophilic membrane filter ("final membrane").

The subject invention further pertains to a steam sterilizable multi-element filter assembly comprising a housing, preferably of sterilizable polymer having inlet and outlet portions, the inlet portion including an inlet port and the outlet portion including an outlet port, the inlet and outlet portions defining a flow channel between the inlet and outlet ports; one or more prefilter(s) retained within the housing fully extending across the flow channel, the prefilter(s) disposed closer to the inlet port than the outlet port; two or more hydrophilic microporous membrane(s) retained within and preferably hermetically sealed to the housing and extending across the flow channel, an intermediate hydrophilic microporous membrane adjacent to the prefilter and disposed closer to the outlet port than the inlet port and at least a final hydrophilic microporous membrane adjacent the intermediate membrane; such that plasma to be purified must pass in order through the prefilter(s), the intermediate hydrophilic microporous membrane, and then the final hydrophilic microporous membrane.

BEST MODE(S) FOR CARRYING OUT THE INVENTION

In the method of purifying plasma according to the subject invention, fresh or frozen plasma is first subjected to customary treatment in which virtually all red blood cells and a substantial portion of white blood cells are removed. Although it is preferable that all leukocytes are removed, this is generally impractical, and it is understood that the plasma to be purified will contain a small but finite number of leukocytes.

In operation, the blood plasma flows by gravity, i.e., preferably at a head of from 15 inches to 48 inches, more preferably about 28 inches, through the leukocyte filtration device, and from thence into a collection vessel, which may be a collection bag or the like. Attachment of the plasma source (i.e. fresh, frozen, etc.) to the filter may be made by conventional means. The particular methods of connection, supply, bypass, post-treatment, etc.) are not required for an understanding of the method of removing leukocytes from plasma or the device suitable therefor as claimed herein.

Figure 1:
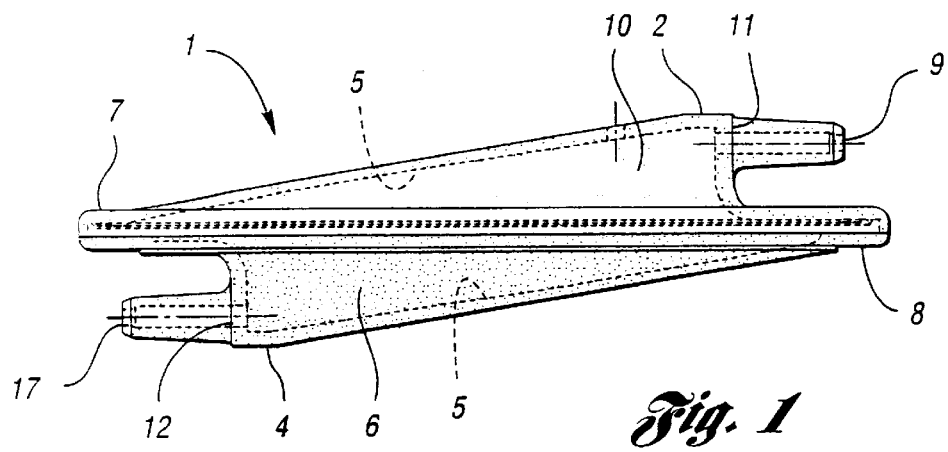
FIG. 1 illustrates a side view of an assembled filter of one embodiment of the subject invention.

FIG. 1 illustrates one embodiment of the subject multi-component filter. Other variations will readily suggest themselves to one skilled in the art. In FIG. 1, filter 1 consists of two injection molded portions, an inlet portion 2 and an outlet portion 4. In plan, the device is substantially rectilinear, preferably with rounded corners. However, the shape of the device is not critical, and the device shape as well as filter configuration may be adapted as required for any given application. A flow channel is formed by the interior wall of outermost surfaces 5 of the device, which rise at a modest angle, e.g., 5–15°, preferably 9–10° from the end 7 of the inlet portion most removed from the inlet 9 and the end 8 of the outlet portion most remote from outlet 17. The flow channel of the device comprises the enclosed volume including inlet flow channel 10 and outlet flow channel 6, respectively. The ramps formed by the rising outermost surfaces are terminated by substantially vertical walls 11 and 12 on which inlet 9 and outlet 17 are located.

Figure 2A:
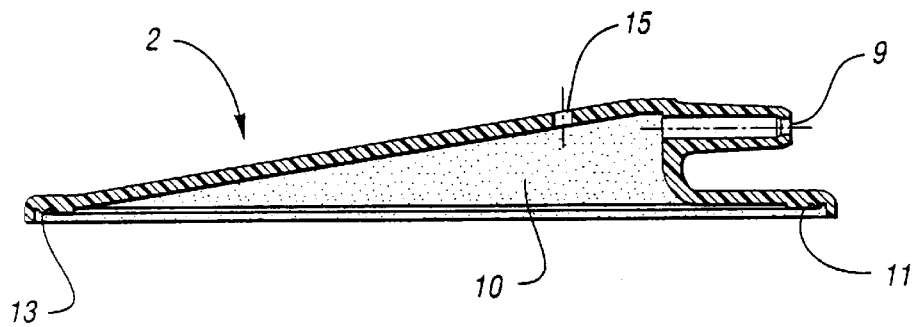
FIG. 2a illustrates a side view of the inlet portion of one embodiment of a filter device prior to assembly.
Figure 2B:
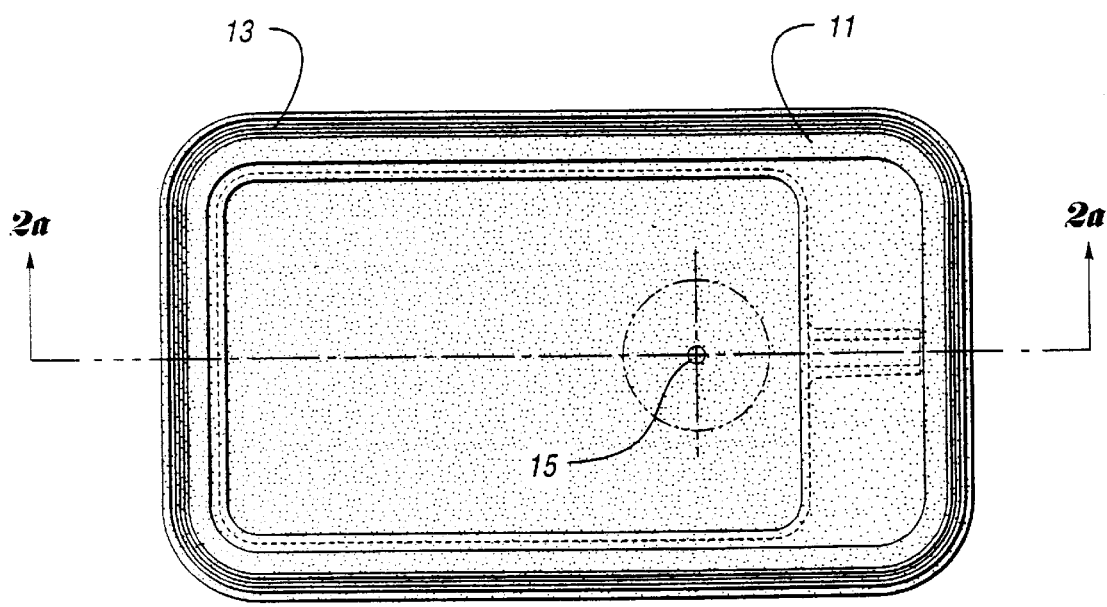
FIG. 2b illustrates a view in plan of the inlet portion of one embodiment of a filter device according to the present invention, from the direction of the sealing surfaces.

FIG. 2a illustrates a side view of the inlet portion 2 of one embodiment of the subject filter device across section 2a of FIG. 2b. At 9 is the inlet through which plasma to be treated flows into inlet flow channel 10. At 11 is a raised annular portion 11 which forms a seal, for example a compression seal, against the filter(s) when the device is assembled. At 13 is a raised annular rib of generally triangular cross-section, which is used to seal the inlet portion 2 of the device to outlet portion 4 (FIGS. 1, 3a, 3b, 4). Shown at 15 is an optional vent hole which will be plugged or covered by a microporous hydrophobic membrane to allow air to escape the device but not liquid.

Referring to FIG. 2b, viewed from the direction of the sealing surfaces, the perimeter of the inlet portion of the device is substantially planar and is surrounded by a raised annular portion 11 which serves to compress and/or seal the periphery of the prefilter(s). Spaced apart from the raised annular portion 11 is a raised annular rib 13 which serves as a pressure concentrating structure when pressed against the corresponding raised annular mating surface 23 (FIGS. 3a, 3b, 4) of the outlet portion of the device. Other sealing arrangements will readily suggest themselves to one skilled in the art. At 15 is an optional vent hole which is hermetically sealed to a polytetrafluoro-ethylene or other microporous venting material, preferably hydrophobic, with a nominal pore size of 0.02 μm.

Figure 3A:
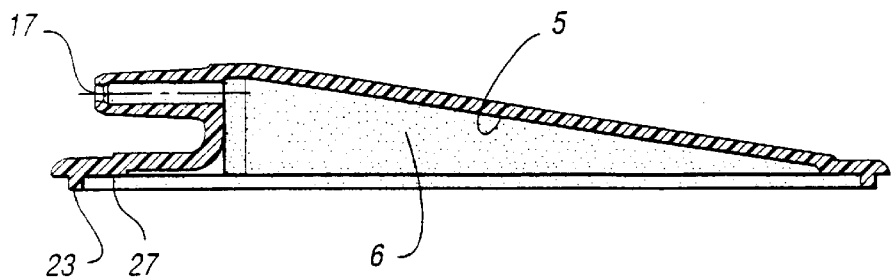
FIG. 3a illustrates a side view of the outlet portion of one embodiment of a filter device prior to assembly.
Figure 3B:
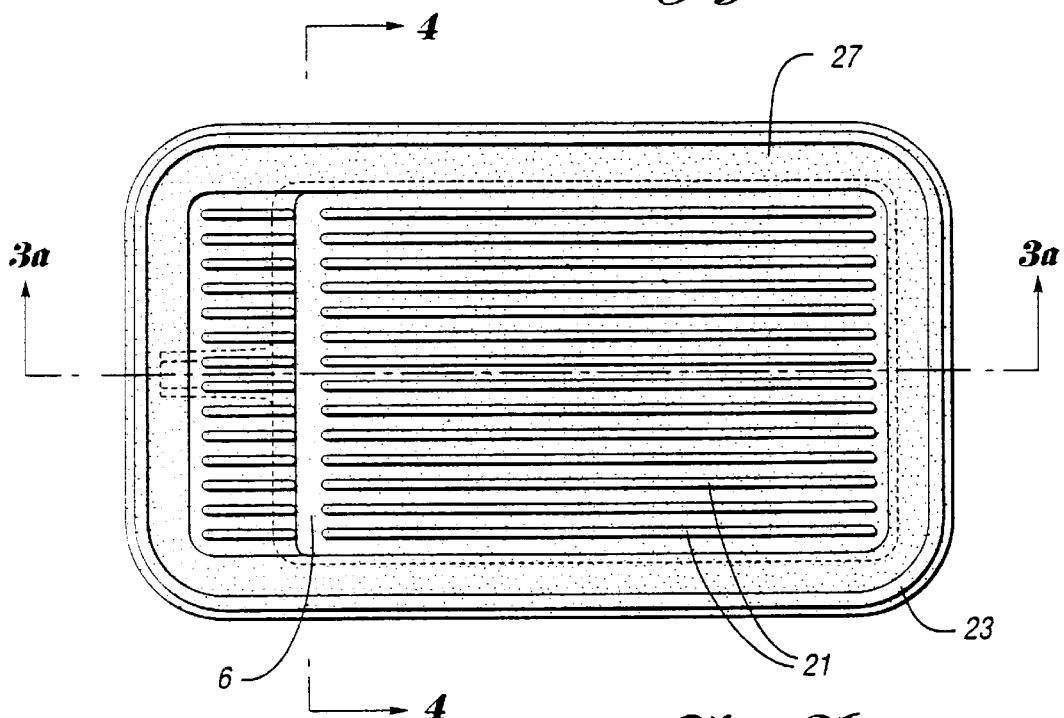
FIG. 3b illustrates a view in plan of one embodiment of a filter device according to the present invention, from the direction of the sealing surfaces.

FIG. 3a is a side view across section 3a of FIG. 3b. The outlet is shown at 17. Raised annular mating surface 23 mates with corresponding raised annular rib 13 (FIGS. 2a, 2b) and is subsequently sealed to the rib 13, preferably by ultrasonic bonding techniques. The outlet channel is shown at 6. The outlet channel is formed by the space enclosed by the interior wall 5 of the outermost surface and the surface of the hydrophilic microporous membranes 25a and 25b (FIG. 5), which will be sealed to sealing surface 27.

Referring to FIG. 3b, the outlet portion of a device is shown in plan. Preferably, the outlet channel 6 contains a plurality of ribs 21 rising from the interior wall of the outermost surface forming a support member for the filter(s), as shown in section in FIG. 4. The ribs generally rise to the plane of the lowermost surface of the filter membrane and provide support to ensure the filter is not deformed, ruptured, or separated from its seal with the device during filtering. Other support members, i.e. screens, perforated plates, and the like may be used as well. If the filter is to be used in low pressure drop applications only, e.g., gravity feed, the support member may be eliminated.

Surrounding the outlet channel is raised annular mating surface 23, which, together with raised annular rib 13 (FIGS. 2a, 2b), provide a means for hermetically sealing the device, for example by ultrasonic welding. Prior to assembly of the device, primary hydrophilic microporous membranes 25a and 25b (FIG. 5) is hermetically sealed to annular membrane sealing surface 27, for example by heat sealing. Following sealing of the hydrophilic microporous membranes, prefilter 29 (FIG. 5) is placed in position atop the membranes and inlet portion 1 is placed atop outlet portion 2 and the assembly bonded together, preferably by ultrasonic welding.

Figure 4:
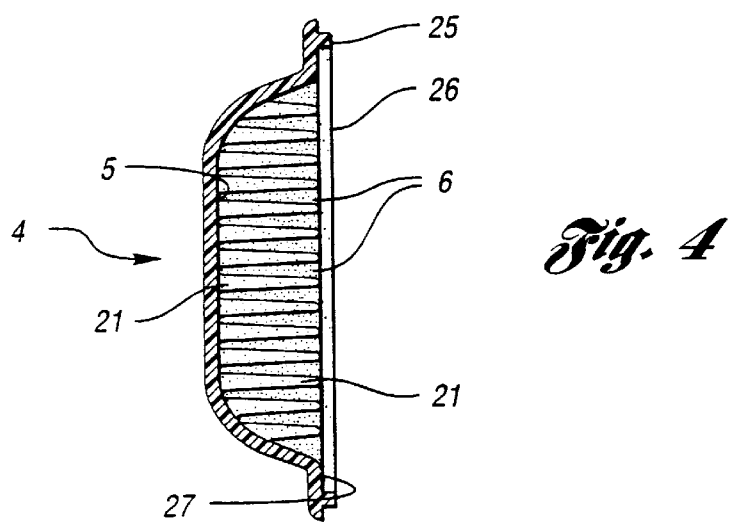
FIG. 4 is a cross-section of the outlet portion of a filter device across section 4—4 of FIG. 3b.

Referring to FIG. 4, the outlet portion of the device is shown across section 4—4 of FIG. 3b. The outlet channel 6 and ribs 21 may be clearly seen. At 26 are the hydrophilic membranes abutting the ribs and the prefilter(s), both shown as a single unit for clarity. The membrane sealing surface 27, exterior wall 5, and raised annular mating surface 23 are also shown.

Figure 5:
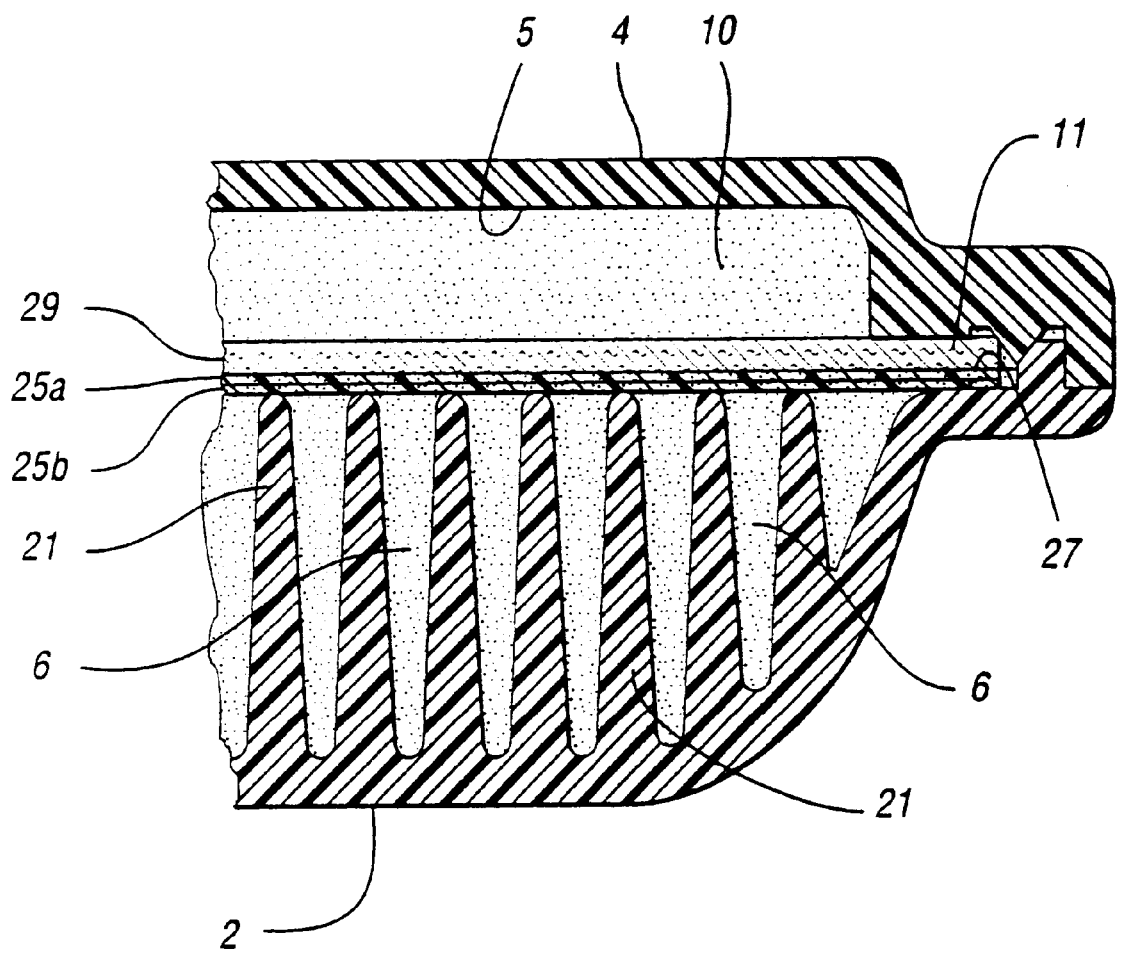
FIG. 5 is a detail view of area D of FIGS. 2 and 3.

FIG. 5 illustrates the placement of the final microporous hydrophilic membrane 25b, intermediate microporous hydrophilic membrane 25a, prefilter 29, and the relative geometries of the various annular surfaces when the device is assembled. The hydrophilic microporous membranes 25a and 25b are sealed, preferably heat sealed, to sealing surface 27, and supported across outlet channel 6 by ribs 21. The prefilter 29 is trapped between the portion of the intermediate hydrophilic microporous membrane atop sealing surface 27 and annular raised portion 11. Raised annular rib 13 has been deformed in the heat sealing process to form a unitary structure with raised annular mating surface 23. The plasma flow is through the inlet 9 into inlet channel 10, through prefilter 29, intermediate membrane 25, and final membrane 25 into outlet channel 6 and from there to outlet 17 (FIG. 1).

In use, the inlet 9 is connected to a plasma supply source, which may supply plasma by gravity flow or under pressure, i.e., through use of a peristalic-type or plunger-type pump. Air is displaced through optional vent 15 and the plasma passes through the prefilter 29 and then through the hydrophilic microporous membranes 25 and 26. The prefilter is a "depth-type" prefilter, and thus the majority of macrocytes and granulocytes and any other large particulates may be trapped by the prefilter without significantly decreasing its flow rate. Of the leukocytes or particulates which pass through the prefilter, the vast majority, virtually, and many times, all of the leukocytes, are prevented from passing into the treatment bag by the intermediate hydrophilic, leukocyte trapping microporous membrane. Any leukocytes, e.g., those of extremely small size which pass through the intermediate membrane are virtually fully retained by the final membrane, and hence, the plasma passing through the filter will be substantially leucocyte-free, providing the pressure across the filter is not so high as to cause it to separate from the housing or rupture, or to deform the leukocytes to such an extent that they are forced through the fine pores of the final membrane. To ensure that the latter event does not occur, the maximum pore size of the final membrane is selected so as to be considerably smaller than the minimum leucocyte diameter. It is most desirable to remove leukocytes such that their concentration in the plasma is reduced by a factor of at least $10^3$, preferably $10^4$. Most preferably, the final leukocyte concentration is 0.

The prefilter performs the function of removing large particulates and gelatinous substances so as to prevent clogging of the intermediate filter. The prefilter also may remove a substantial portion of large leukocytes, i.e. macrocytes and granulocytes. The intermediate membrane removes the most substantial portion of smaller leukocytes such that plasma exiting the intermediate membrane has had preferably greater than 90% of leukocytes removed. The final membrane has smaller pores than the intermediate membrane, and ensures that virtually no leukocytes remain in the completely filtered plasma.

With regard to pore size, the pore size and type must be selected with the function of the particular filter element in mind. For the prefilter, for example, a relatively large pore size is selected for rapid filtration yet which will retain substantially all large particulates. When the prefilter is a membrane-type depth prefilter, for example, the preferred pore size is from about 3 µm to about 10 µm. This relatively large pore size is necessary since the pore size range of membrane filters is ordinarily well controlled. However it is preferred that the prefilter comprise a non-woven depth-type filter. Such filters are available from numerous sources, and may consist, for example, of fiberglass, spun bonded or melt blown polypropylene, polyester, and the like, and may have a nominal, or "average" pore size of from about 0.5 µm to about 5 µm. The smaller average pore size is a reflection of the relatively wide pore size range of such materials and the alternative fluid flow paths which depth-type filters present. The most preferable prefilter is a non-woven fiberglass prefilter available from Hollingsworth & Vose as HB-5341 glass filter medium.

The intermediate membrane filter is a hydrophilic membrane filter which has a pore size range sufficiently small that in combination with the prefilter, greater than 80% of leukocytes, more preferably greater than 90% of leukocytes, and most preferably in excess of 95% of leukocytes are retained by the combination of prefilter and intermediate membrane. In other words, the intermediate membrane will pass no more than 20% of leukocytes, preferably no more than 10%, and most preferably no more than 5%. It is yet more preferable that not more than about 1% of leukocytes pass through the intermediate membrane. The pore size of the membrane may vary somewhat, but is preferably in the range of about 0.9 to about 2.0 µm, more preferably in the range of 0.9 to about 1.5 µm. The composition of the intermediate membrane is not overly critical, so long as the membrane is hydrophilic. Thus, intrinsically hydrophobic membranes which have been treated to render their surface hydrophilic are suitable, as are also intrinsically hydrophilic membranes. Membranes may be made of polyacrylates, nylon, polyvinylidene fluoride, polypropylene, polysulfone, polyethersulfone, cellulose acetate, or nitrocellulose. Charged membranes are suitable as well. Nylon membranes are well suited for use herein. A particularly preferred membrane is SUPOR® 1200, a polyethersulfone microporous membrane with a nominal pore size of 1.2 µm available from Gelman Sciences, Inc., Ann Arbor, Mich.

The final membrane is selected so as to render the plasma filtrate substantially leukocyte-free. While the intermediate filter might be selected so as to provide leukocyte-free plasma by utilizing a smaller pore size, use of a smaller pore intermediate membrane without a final membrane possesses two distinct disadvantages. First, the smaller pore size would reduce flow shortly after the onset of filtration due to its pores becoming clogged with leukocytes. Second, were leukocytes to pass through the pores, e.g. by the well known distortion of the leukocyte, or by accidental damage affecting the membrane integrity, then the risk of leukocyte-containing plasma, although small, would be significant.

Thus, the final filter is selected so as to provide a pore size small enough to ensure substantially complete leukocyte removal. Since the vast majority of leukocytes and larger particulates and gels have been removed by the prefilter and the intermediate membrane filter, the small pore size of the final membrane will not overly slow the filtration rate. As is the case with the intermediate membrane, the final membrane is hydrophilic, and may be a charged membrane as well. The pore size range of the final membrane is from about 0.3 to about 1.5 µm, and preferably is of a smaller or equal pore size than the intermediate membrane. A pore size range of 0.4 µm to 1.0 µm is suitable, and a range of 0.7 µm to 1.0 µm is preferred. Particularly suitable is a SUPOR® polyethersulfone microporous membrane with a nominal pore size of 0.8 µm.

The surface area, or effective filtration area (EFA) of the filter may be adjusted according to the volume of plasma to be filtered and the desired flow rate. For example, the subject device has been illustrated with reference to a planar, substantially rectangular filter capsule. However other shapes are useful as well, including pleated cylindrical filters, spiral wound cylindrical filters, and the like, provided the subject filter stack is used. The internal volume should be minimized so that retention of plasma by the filter itself is as small as possible. In general, a minimum flow rate of 1 to 10 ml/min/cm$^2$ at 1 psi or thereabouts is desired, more preferably a minimum flow rate of 2–3 ml/min/cm$^2$. Higher flow rates are, of course, desired. The filter should preferably be capable of filtering a minimum of 300 ml of human plasma before the flow rate decreases to such an extent that the filter may be considered to be "plugged". The filtration efficiency should be such that a $10^4$ reduction of leukocytes from conventionally prepared plasma containing a normal leukocyte concentration of is possible. In the most preferable case, no leukocytes will be present in the filtrate. With the preferred devices according to the present invention, incorporating at least one prefilter and intermediate and final hydrophilic microporous membranes, suitable filter areas are not particularly limited. For example, cartridge filters with pleated or spiral elements may be designed for large volume filtration, while small units may be provided for filtration of single plasma units. In the latter case, for example, a suitable filter size has an EFA of from 15 to 20 cm$^2$. However, units with EFAs of from 0.1 m$^2$ to several m$^2$ or larger are also feasible.

The prefilter material should meet USP requirements for particle shedding and Class VI toxicity requirements. Preferably, the material further meets European community toxicity requirements as well.

Combinations of various prefilters with the same or different pore sizes are also useful. In general, hydrophobic materials such as polypropylene should be treated with a hydrophilizing agent to render the material hydrophilic. Such agents are known to those skilled in the art. The intermediate and final hydrophilic microporous membranes are preferably ones which can be heat-sealed to the filter housing by conventional techniques such as ultrasonic bonding. Membranes which may be adhesively bonded or solvent bonded are also acceptable.

As indicated previously, the hydrophilic microporous membranes may be intrinsically hydrophilic or may be hydrophobic membranes surface treated to render them hydrophilic. While the membrane may also include negatively charged sites to aid in leucocyte retention, it is most important that the pore size be such that the pore size alone substantially prevents passage of leukocytes. Hydrophilic microporous membranes of suitable pore size are commercially available, and may be manufactured by processes disclosed in U.S. Pat. Nos. 3,876,738; 4,340,479; 4,473,474; 4,673,504; 4,708,803; 4,711,793; 5,076,935; 4,900,449; 4,964,990; and 5,108,607, which patents are herein incorporated by reference. Preferred hydrophilic microporous membranes are Supor® microporous membranes available from Gelman Sciences.

The housing for the multicomponent filter assembly of the subject invention are preferably prepared from injection molded polymer. The polymer may be a thermoplastic or thermosetting polymer, and should be sterilizable. Moreover, the polymer must not elute toxic metals, oligomers, monomers, or catalysts in the presence of aqueous solutions. Finally, although heat-sealable or solvent-bondable thermoplastics may be used, it is preferable that the polymer be capable of being sealed by ultrasonic or RF welding techniques. Among the suitable polymers are the amorphous polyamides, high temperature polyacrylics and polyesters, and most preferably, the polycarbonates. A preferred polycarbonate is MAKROLON 2658-1112 Natural, available from Miles, Inc.

A series of plasma purifying screening tests were run using conventionally prepared bovine serum and a 28 inch head height. For the purposes of the tests, a 47 mm stainless steel filter holder was utilized to hold the primary membrane and prefilter(s). Unfiltered bovine serum was obtained from American Biologic Tech., Inc.

As a result of these screening tests, it was discovered that the selection of suitable prefilters and membrane filters was not straight-forward. A single membrane of 1.2 $\mu$m polyethersulfone plugged virtually immediately. When employed with a prefilter, suitable flow rates could be achieved with "clean" plasma with certain prefilters, however with other plasma samples, plugging occurred rapidly. Some of the many combinations tried exceeded acceptable levels of particle shedding, leaching of heavy metals, or were of high pH. These tests showed that a two-stage (prefilter plus single membrane) is unsuitable, and that a minimally three stage filter stack, including a depth-type prefilter, was necessary.

Testing of plasma (leukocyte-removal) filter devices was performed in a sterile-barrier laminar-flow hood under strict aseptic techniques, with minimal handling of plasma units. Leukocyte-removal filter devices were composed of glass fiber/Supor® 1200/Supor® 800 membranes, with an effective filtration area (EFA) of 17 cm$^2$. Human plasma was obtained frozen from the Red Cross, and maintained in a frozen state until the morning of testing. Plasma was thawed using a circulating water bath at constant temperature of 8° C. Plasma from four individual units (ranging in volume from 255 mL to 410 mL) was pooled together in a 3-L sterile collapsible admixture bag, after which testing was performed as soon as possible (less than 30 minutes). Plasma was delivered from the collapsible bag, at 28 inch head height, through a Medical Specialties 103 inch vented administration set.

Four leukocyte-removal filter devices, labeled M1, M2, M3 and M4, were filtered into luer-lock extension sets (total length=6 inches), which were then fitted to the previously mentioned administration set. (Due to air embolus occluding device M1, only data from the other three devices are reported.) Amounts of plasma delivered through filter devices at time intervals of 10 seconds, 1, 2, 5, 10, 15, 20, 25 and 30 minutes were measured and recorded. Plasma flow was continuous and uninterrupted. After completion of testing, plasma samples were treated as biohazard, then sterilized (through autoclaving at 121° C. for 30 minutes) and properly disposed of. All materials used in testing were likewise sterilized, and disposed of if necessary. Flow data is presented in Table 1.

TABLE 1

Volumes (Cumulative and Per Time Interval) and Flow Rates of Human Plasma
@ 28" Head Height Filtered Through 17-cm$^2$ Leukocyte-Removal Filter Devices

| Time | Device M2 | | | Device M3 | | | Device M4 | | | Average | | | Vol/time/unit area |
|---|---|---|---|---|---|---|---|---|---|---|---|---|---|
| (min) | Vol | Cum Vol | Rate | Vol | Cum Vol | Rate | Vol | Cum Vol | Rate | Vol | Cum Vol | Rate | (mL/min/cm2) |
| 0.17 | 13.4 | 13.4 | 80.4 | 13.5 | 13.5 | 81.0 | 11.0 | 11.0 | 66.0 | 12.6 | 12.6 | 75.8 | 4.46 |
| 1 | 51.0 | 64.4 | 61.2 | 54.0 | 67.5 | 64.8 | 43.1 | 54.1 | 51.7 | 49.4 | 62.0 | 59.2 | 3.48 |
| 2 | 36.0 | 100.4 | 36.0 | 53.2 | 120.7 | 53.2 | 28.5 | 82.6 | 28.5 | 39.2 | 101.2 | 39.2 | 2.31 |
| 5 | 42.0 | 142.4 | 14.0 | 85.8 | 206.5 | 28.6 | 34.5 | 117.1 | 11.5 | 54.1 | 155.3 | 18.0 | 1.06 |
| 10 | 36.9 | 179.3 | 7.4 | 59.0 | 265.5 | 11.8 | 39.0 | 156.1 | 7.8 | 45.0 | 200.3 | 9.0 | 0.53 |
| 15 | 31.8 | 211.1 | 6.4 | 39.0 | 304.5 | 7.8 | 19.5 | 175.6 | 3.9 | 30.1 | 230.4 | 6.0 | 0.35 |
| 20 | 26.0 | 237.1 | 5.2 | 34.0 | 338.5 | 6.8 | 24.0 | 199.6 | 4.8 | 28.0 | 258.4 | 5.6 | 0.33 |
| 25 | 24.0 | 261.1 | 4.8 | | | | | | | | | | |
| 30 | 24.5 | 285.6 | 4.9 | | | | | | | | | | |

Note: Units for volume (Vol) and cumulative volume (Cum Vol) are reported in mL. Units for rate are reported in mL/min.
The average cumulative volume of human plasma delivered through the leukocyte-removal filter devices was 258.4 mL. The average volume of human plasma delivered per time per unit of EFA (mL/min/cm$^2$), based on the results of this experiment, was 2.31 mL/min/cm$^2$. This number represents average value at 48.3% flow decay, following delivery of 100-mL plasma after two minutes of flow.

While the best mode(s) for carrying out the invention have been described in detail, those familiar with the art to which this invention relates will recognize various alternative designs and embodiments for practicing the invention as defined by the following claims.

What is claimed is:

1. A method for purifying blood plasma which has been treated to remove erythrocytes and a substantial portion of leukocytes, an initial concentration of leukocytes remaining, comprising:

passing said blood plasma through a disposable multicomponent filter, said multicomponent filter comprising a filter stack containing one or more depth-type prefilters having a nominal pore size of from about 0.5 $\mu$m to about 5 $\mu$m, at least one intermediate hydrophilic microporous membrane filter having a maximum nominal pore size of less than about 3 $\mu$m; and at least one final hydrophilic microporous membrane filter having a nominal pore size of from about 0.3 $\mu$m to about 1.2 $\mu$m, the nominal pore size of said final hydrophilic microporous membrane smaller than the nominal pore size of said intermediate hydrophilic microporous membrane, said filter stack contained in a housing, said final hydrophilic microporous membrane sealed to said housing, said housing further comprising a hydrophobic membrane, one side of said hydrophobic membrane communicating with an inside of said housing, one side of said hydrophobic membrane communicating with an outside of said housing wherein the leukocyte concentration present in said blood plasma after passing through said filter is substantially reduced from its initial concentration.

* * * * *